United States Patent [19]

Hurst

[11] Patent Number: 5,205,298
[45] Date of Patent: Apr. 27, 1993

[54] METHOD AND APPARATUS FOR USE IN APPLYING ELASTOMERIC COVERINGS TO BODY

[76] Inventor: Carroll Hurst, P.O. Box 741, Granbury, Tex. 76048

[21] Appl. No.: 799,050

[22] Filed: Nov. 26, 1991

[51] Int. Cl.$^5$ ............................................. A61F 6/04
[52] U.S. Cl. .................................. 128/844; 128/842; 206/69; 604/349
[58] Field of Search ............... 128/842, 843, 844, 917, 128/918, 830; 604/349; 206/69

[56] References Cited

U.S. PATENT DOCUMENTS

| | | | |
|---|---|---|---|
| 4,840,187 | 6/1989 | Brazier | 128/844 |
| 4,872,463 | 10/1989 | Nishizono | 128/844 |
| 4,875,491 | 10/1989 | Parrone | 128/844 |
| 4,917,113 | 4/1990 | Conway | 128/844 |
| 4,961,734 | 10/1990 | Kassman | 128/844 |
| 4,972,850 | 11/1990 | Broad, Jr. | 128/842 |
| 4,984,582 | 1/1991 | Romaniszyn | 128/844 |

Primary Examiner—Robert A. Hafer
Assistant Examiner—David Kenealy
Attorney, Agent, or Firm—Geoffrey A. Mantooth

[57] ABSTRACT

The apparatus includes a bellows member formed by a pleated wall. An interior cavity is located inside of the bellows member. The wall has first and second openings that communicate with the interior cavity. A lip surrounds the first opening. To use the apparatus, the elastomeric covering is inserted, closed end first, into the interior cavity. The open end of the covering is folded onto the lip at the first opening so as to form a seal. The bellows member is contracted to expel air through the second opening. Then, the second opening is closed and the bellows member is expanded, causing the covering to expand. The body member is inserted into the interior of the covering. The second opening is then opened, allowing the covering to contract onto the body member.

13 Claims, 2 Drawing Sheets

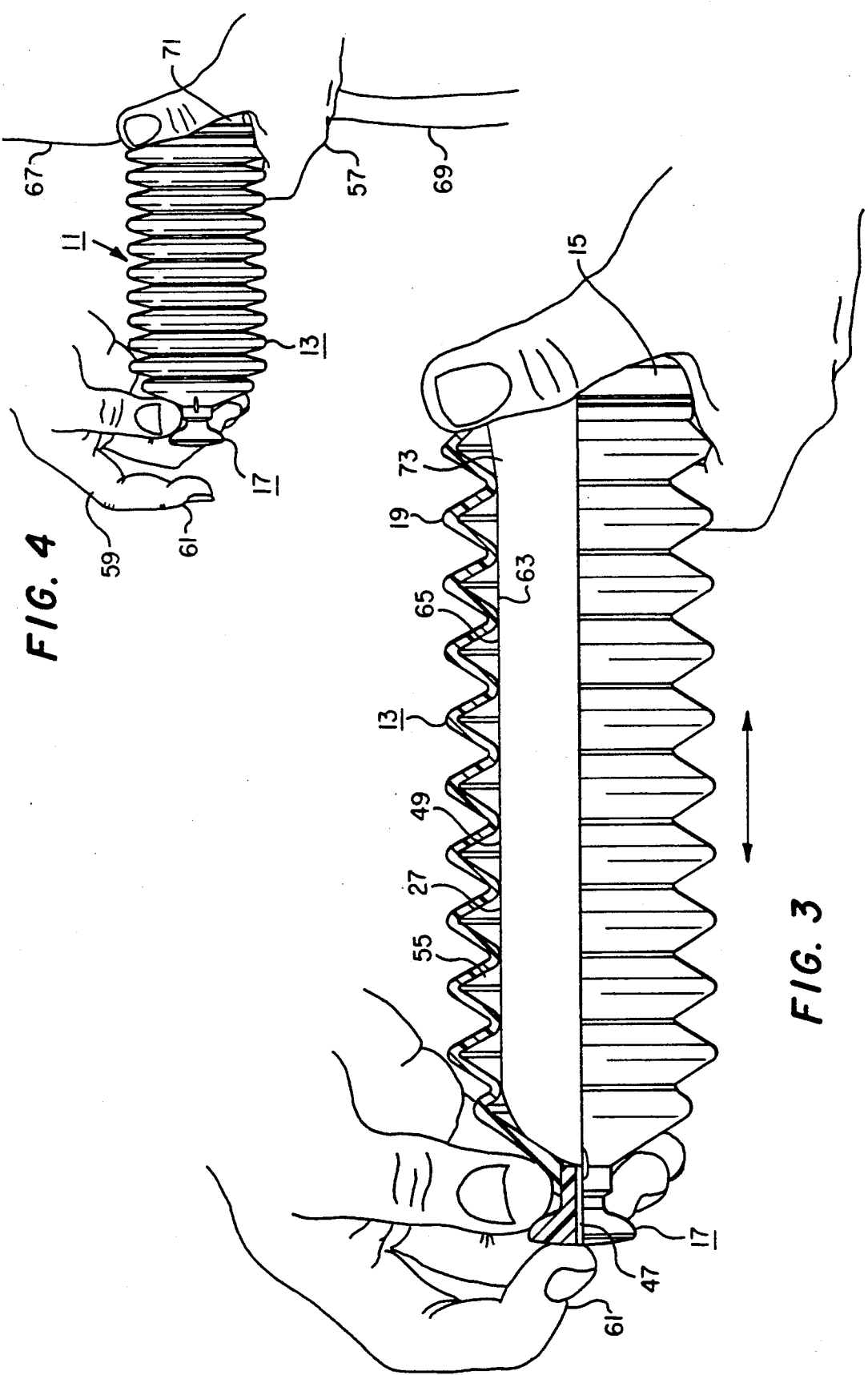

METHOD AND APPARATUS FOR USE IN APPLYING ELASTOMERIC COVERINGS TO BODY

FIELD OF THE INVENTION

The present invention relates to methods and apparatuses for the application of elastomeric coverings to body members, such as for example, applying a condom onto a penis.

BACKGROUND OF THE INVENTION

Condoms are worn over the penis during sexual intercourse to provide a measure of protection of birth control and to protect against the transmission of disease. Condoms, which are made of elastomeric material, are designed for a close fit. This makes it somewhat difficult to put on a condom without pulling the skin or hair.

It is an object of the present invention to provide a method and an apparatus for simplifying the application of a condom.

BRIEF DESCRIPTION OF THE DRAWINGS

FIG. 3 is a schematic longitudinal partial cross-sectional view, showing the apparatus and the condom in an expanded condition.

FIG. 4 is a view showing the apparatus being used to apply a condom onto a human.

DESCRIPTION OF PREFERRED EMBODIMENT

The apparatus of the present invention is used to apply a condom onto a penis. The condom is made of an elastomeric material that is easily expanded. The apparatus takes advantage of this characteristic to momentarily expand the condom to a size where the penis can be comfortably inserted into the condom. After the penis has been inserted into the condom, the apparatus then allows the condom to contract onto the penis, wherein the apparatus is removed.

Figure 1:
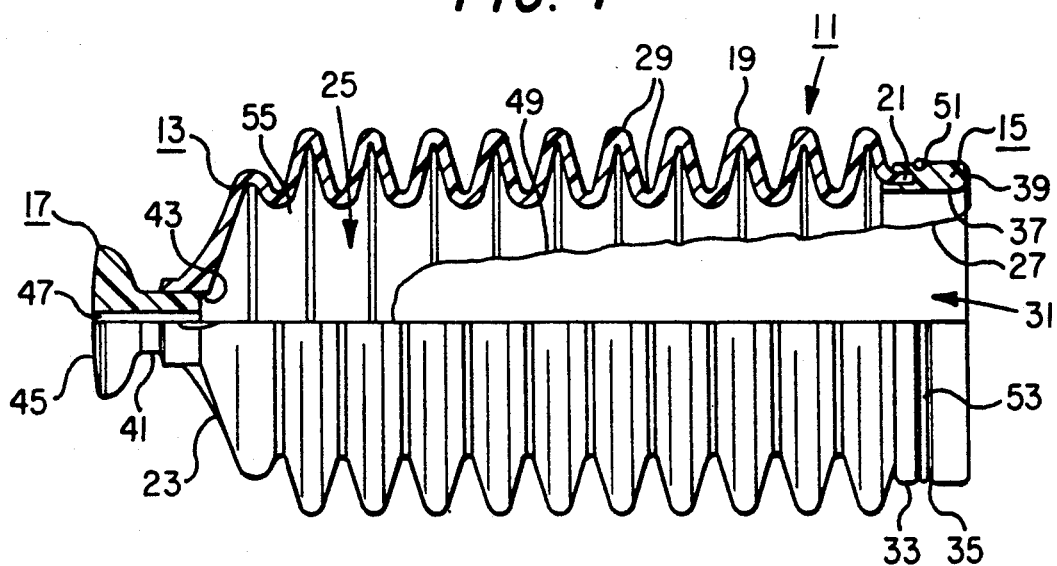
FIG. 1 is a longitudinal partial cross-sectional view of the apparatus of the present invention, in accordance with a preferred embodiment, showing the apparatus in the relaxed condition and showing a condom located therein.

In FIG. 1, there is shown a longitudinal partial cross-sectional view of the apparatus 11 of the present invention, in accordance with a preferred embodiment. The apparatus 11 of the present invention includes a bellows member 13, a lip ring 15 and a handle 17.

The bellows member 13 is formed by a wall 19 that extends between first and second ends 21, 23. Inside of the member 13 is an interior cavity 25. The wall 19 extends circumferentially around the interior cavity 25. The member 13 and the interior cavity 25 are generally cylindrical in shape so as to approximate the shape of the condom 27.

Figure 2:
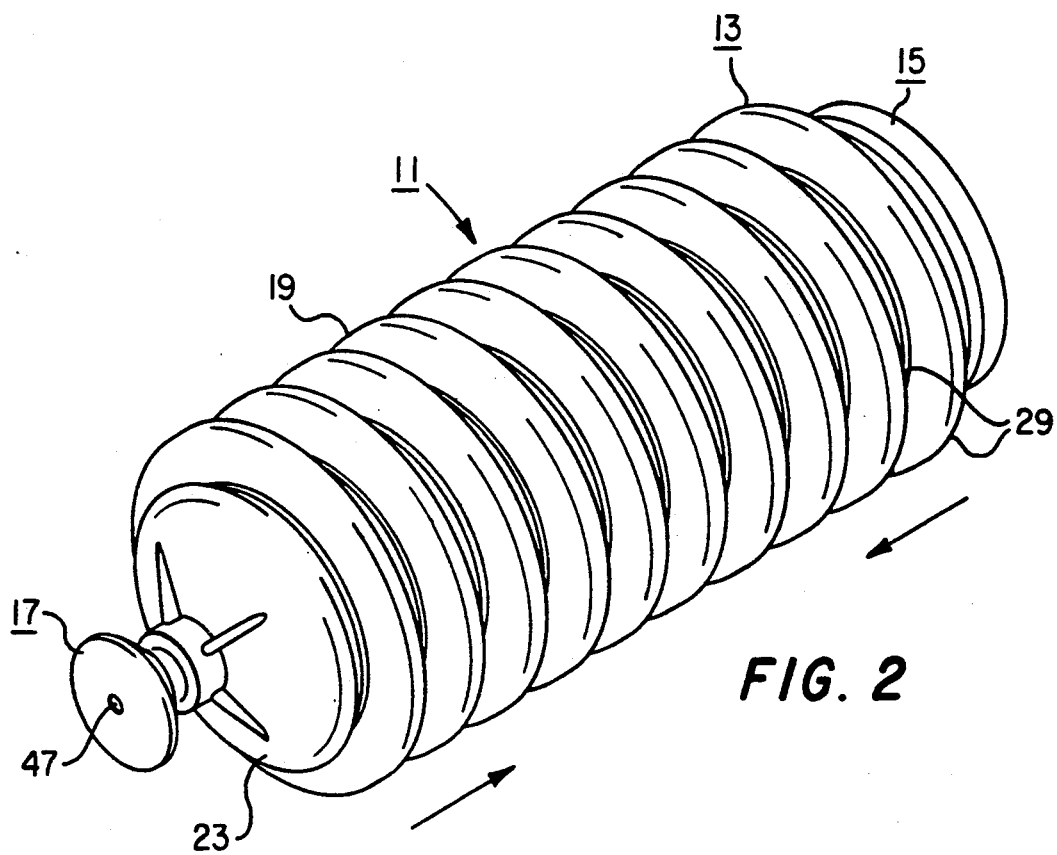
FIG. 2 is an isometric view of the apparatus.

The wall 19 is pleated 29 so as to form a bellows or an accordion member. The pleats 29 are oriented transverse to the longitudinal axis of the member so as to extend circumferentially around the interior cavity 25. Thus, the wall 19 can be expanded and contracted along the longitudinal axis and therefore along the length of the condom and the penis. FIG. 1 shows the bellows member 13 in a relaxed condition. The bellows member can be contracted or compressed along the longitudinal axis, as shown in FIG. 2. In addition, the bellows member can be expanded along the longitudinal axis, as shown in FIG. 3.

The first end 21 of the wall 19 has a first opening 31. Coupled to the wall first end 21 is the lip ring 15, which is annular shaped. The lip ring 15 extends circumferentially around the first opening 31. The first opening 31 and the interior cavity 25 are sized large enough so as to allow the penis to be inserted therein. The lip ring 15 is rigid so as to hold open the open end of the condom during use of the apparatus, as will be explained in more detail below. The lip ring has a smooth exterior surface 33, which exterior surface has a circumferential groove 35 extending around the first opening. The lip ring also has an interior surface 37 and an outer edge 39 that merges with the exterior and interior surfaces. The outer edge 39 is rounded.

The second end 23 of the wall 19 tapers radially inward so as to close off that end of the interior cavity 25. The handle 17 is coupled to the second end 23 of the wall. The shank 41 of the handle 17 is received by an opening 43 in the wall second end 23. The handle 17 extends longitudinally away from the first end 21. The end 45 of the handle has a smooth surface.

A second opening 47 is provided in the second end 23 of the wall 19. In the preferred embodiment, the second opening is formed by a passage 47 that extends through the handle 17 to the interior cavity 25. The passage 47 is of a small diameter so that it can be easily closed.

The wall 19 is made of a plastic or rubber material which is suitable for expanding and contracting like a bellows. The lip ring 15 is made of a rigid plastic and is coupled to the wall 19 using a suitable adhesive. The handle 17 is also made of plastic and is also coupled to the wall using a suitable adhesive.

The use of the apparatus 11 will now be described. First, the condom 27 is located within the interior cavity 25 of the apparatus, as shown in FIG. 1. The condom 27 is made of an elastomeric material and has a closed end portion 49 and an open end portion 51. The closed end portion 49 is located within the interior cavity 25. The open end portion 51 is folded over the outer edge 39 of the lip ring 15. The outer end of the condom 27 is provided with a bead 53. This bead 53 is seated into the groove 35 on the lip ring 15. The groove 35 retains the open end portion 51 of the condom on the lip ring. A seal is formed between the condom open end portion 51 and the lip ring exterior surface 33. The lip ring 15 holds the open end portion 51 of the condom open during use of the apparatus 11.

With the condom 27 installed in the apparatus 11, there is a volume 55 of air between the condom 27 and the wall 19. This volume 55 is reduced by compressing the bellows member 13. The bellows member is compressed by forcing the handle 17 and the lip ring 15 towards each other, as shown in FIG. 2. The second opening 47 in the handle 17 is uncovered so as to allow air to escape from the volume 55 to the exterior. The bellows member 13 is easily manipulated by grasping the lip ring 15 with one hand 57 and grasping the handle 17 with the other hand 59 (see for example FIG. 4).

Then, the second opening 47 is closed by placing a finger 61 over it as shown in FIG. 3. The bellows member 13 is then expanded by pulling the handle and the lip ring apart. This action causes the condom 27 to expand because the air pressure acting on the interior surface 63 of the condom is greater than the air pressure acting on the exterior surface 65 of the condom.

With the condom 27 expanded, the apparatus is brought close to the body (see FIG. 4 which shows the abdomen 67 and legs 69 of a human male) and the penis 71 is inserted, glans end first, into the interior 73 of the condom. After the penis has been inserted, the second opening 47 is opened by removing the finger 61, as shown in FIG. 4. This allows air to enter the volume 55, thereby allowing the condom to contract onto the penis. The open end portion 51 of the condom is then rolled off of the lip ring 15. The apparatus, which returns to its relaxed condition, is then removed.

To simplify manufacturing, the apparatus can be molded and formed from one piece. Thus, the wall, the lip ring and the handle could all be molded out of one piece. The bellows member can be molded in any relaxed condition. For example, the bellows member can be molded such that when the bellows member is relaxed, it is elongated as shown in FIG. 3. To use the apparatus, the bellows member is then contracted and expanded as appropriately needed to expand and contract the condom.

Although the apparatus of the present invention has been described as being used for condoms, other types of elastomeric coverings can be applied to other body parts with the apparatus. For example, condom catheters are easily applied with the apparatus of the present invention. A condom catheter is a condom with a catheter tube extending out of the end of the condom. Condom catheters are frequently used when an ordinary catheter that is inserted into the urinary tract of a patient cannot be used. The condom portion of the catheter secures the catheter tube to the penis. Prior art methods of installation of condom catheters are difficult and even painful for patients. The apparatus of the present invention allows the application of a condom catheter in a fast and painless manner. In addition to condom catheters, the apparatus can be used to install surgical gloves onto hands.

The foregoing disclosure and the showings made in the drawings are merely illustrative of the principles of this invention and are not to be interpreted in a limiting sense.

I claim:

1. An apparatus for use in applying an elastomeric covering to a body member, comprising:
   a) a hollow member being formed by a wall and having an interior cavity for receiving said covering;
   b) said wall having a first opening that communicates with said interior cavity, said first opening being sized large enough so that said body member can be inserted through said first opening, said wall having a lip that surrounds said first opening, said lip being adapted for receiving and retaining a portion of said covering;
   c) said interior cavity having a volume, said wall being expandable and contractible so as to change the volume of said interior cavity, said wall having means automatically and resiliently for returning said wall to a relaxed condition from an expanded or contracted condition;
   d) said wall having a second opening that is separate and apart from said first opening, said second opening communicating with said interior cavity, said second opening being capable of being opened and closed.

2. The apparatus of claim 1 wherein said lip has a circumferential groove located on a surface that is exterior to said interior cavity, said groove for retaining said covering onto said lip.

3. The apparatus of claim 2 wherein said covering has a shape, said interior cavity has a shape that approximates the shape of said covering.

4. The apparatus of claim 2 further comprising handle means for use in expanding and contracting said wall, said handle means extending out from said wall.

5. The apparatus of claim 1 further comprising handle means for use in expanding and contracting said wall, said handle means extending out from said wall.

6. The apparatus of claim 5 wherein said second opening is located within said handle means.

7. An apparatus for use in applying a condom onto a body member, comprising:
   a) an elongated hollow member being formed by a wall and having an interior cavity for receiving said covering, said interior cavity having a volume, said wall extending between first and second ends and around a circumference of said interior cavity such that said wall encompasses said interior cavity;
   b) said wall having a first opening located at said first end, said first opening communicating with said interior cavity, said first opening and said interior cavity being sized large enough so that said body member can be inserted through said first opening, said first end of said wall having a lip that extends circumferentially around said first opening, said lip being rigid so that an open end of said condom can be located around said lip;
   c) said wall having pleats that extend circumferentially around said interior cavity such that said wall can be contracted and expanded to respectively contract and expand the volume of said interior cavity, said wall having means for automatically and resiliently returning said wall to a relaxed condition from an expanded or contracted condition;
   d) said wall having a second opening located at said second end, said second opening communicating with said interior cavity, said second opening being capable of being opened and closed.

8. The apparatus of claim 7 wherein said lip has a circumferential groove located on a surface that is exterior to said interior cavity, said groove for retaining said covering onto said lip.

9. The apparatus of claim 7 further comprising handle means for use in expanding and contracting said wall, said handle means being coupled to and extending out from said wall second end.

10. A method of applying an elastomeric covering to a body member, said covering having an open end portion and a closed end portion, comprising the steps of:
    a) providing bellows means with an interior volume that can be expanded and contracted, and providing said bellows means with a bypass opening;
    b) inserting said closed end portion of said covering into said interior volume of said bellows means and securing said open end portion of said covering to said bellows means so as to form an airtight seal between said covering open end portion and said bellows means and so as to form a volume of air between said covering and said bellows means, said airtight seal being separate from said opening;
    c) contracting said volume of air between said covering and said bellows means while venting said air in said volume through said opening and then sealing said opening;
d) expanding said bellows means so as to lower the air pressure in said volume of air to expand said covering inside of said interior volume;
e) inserting said body member through said open end portion of said expanded covering;
f) increasing the air pressure in said volume of air to allow said covering closed end portion to contract onto said body member, wherein said body member is covered by said covering;
g) removing said covered body member from said bellows means.

11. The method of claim 10 wherein the air pressure in said volume of air is increased to allow said covering to contract by unsealing said opening.

12. The method of claim 10, further comprising the steps of:
a) sealing said volume of air between said covering and said bellows means by sealing said opening with a finger;
b) increasing the air pressure in said volume of air by uncovering said opening with said finger.

13. The apparatus of claim 9 wherein said second opening is located in said handle means.

* * * * *